United States Patent [19]

Alberti et al.

[11] 4,180,062

[45] Dec. 25, 1979

[54] PORTABLE CHILDBIRTH CHAIR WITH ELECTRONIC MONITORING APPARATUS

[76] Inventors: James Alberti, 106 Richardson Rd., Santa Cruz, Calif. 95066; Helmut Schlosser, 1425 N. Rodeo Gulch Rd., Soquel, Calif. 95073

[21] Appl. No.: 894,901

[22] Filed: Apr. 10, 1978

[51] Int. Cl.² ............................................. A61N 5/04
[52] U.S. Cl. ................................... 128/698; 269/328; 297/16
[58] Field of Search ................. 297/16, 377, 384, 423, 297/427; 269/328; 128/1 RS, 2.05 T, 2.05 S, 2.06 E, 2.06 K

[56] References Cited

U.S. PATENT DOCUMENTS

| 1,947,410 | 2/1934 | Emerson | 297/423 |
|---|---|---|---|
| 2,663,029 | 12/1953 | Whitley et al. | 297/377 |
| 2,696,868 | 12/1954 | Miller | 297/427 |
| 3,100,129 | 8/1963 | Adolphson | 269/328 |
| 3,179,465 | 4/1965 | Roberts | 297/377 |
| 3,318,596 | 5/1967 | Herzog | 269/328 |
| 3,780,725 | 12/1973 | Goldberg | 128/2.05 T |
| 3,802,698 | 4/1974 | Burian et al. | 128/2.05 T |
| 3,807,388 | 4/1974 | Orr et al. | 128/2.05 T |

OTHER PUBLICATIONS

Coleman et al., "American Journal of Medical Electronics", Jul.-Sep. 1964, pp. 192-198.

*Primary Examiner*—William E. Kamm
*Attorney, Agent, or Firm*—Claude A. S. Hamrick

[57] ABSTRACT

A portable childbirth chair including a base having a seat portion and two leg portions extending outwardly therefrom, two leg supports, each one being hingedly attached to a different one of the leg portions, two footrests each one being adjustably attached to a different one of the leg supports, adjustment straps for adjusting the inclination of the leg supports relative the base, a backrest hingedly attached to the seat portion, a backrest support frame extending from the seat portion, and a pair of backrest adjustment rods pivotally attached to the backrest at one end and having other ends adapted to engage apertures formed along the backrest support frame so as to adjust the inclination of the backrest relative the base. The chair may be compactly collapsed for easy shipment and storage by telescoping the backrest support frame into the base, and folding the backrest and the two leg supports over the base. The chair also includes electronic monitoring apparatus.

26 Claims, 10 Drawing Figures

Fig_1

Fig_2

Fig_9

Fig_10

PORTABLE CHILDBIRTH CHAIR WITH ELECTRONIC MONITORING APPARATUS

BACKGROUND OF THE INVENTION

1. Field of the Invention

This invention relates generally to chairs and more particularly to portable and adjustable chairs for supporting a woman during the process of childbirth.

2. Description of the Prior Art

Before the advent of modern medicine, women traditionally gave birth in a squatting position so that gravity might advantageously assist in the birthing process. In more recent years this traditional childbirth position has been replaced by the substantially horizontal position imposed by a modern-day labor table or by a bed.

Furthermore, there has been a recent and accelerating trend towards giving birth at home or in other nonclinical environments. Heretobefore, women wishing to give birth at home had no choice but to lie upon a flat, horizontal bed.

A problem that the prior art does not address is how to provide a device for easing the childbirth process that is portable enough to be transported to a birthing site.

SUMMARY OF THE INVENTION

It is an object of this invention to provide a childbirth chair which can support a woman in nonhorizontal positions so that gravity can assist in the birthing process.

Another object of this invention is to provide a childbirth chair which is lightweight and sturdy, and which folds compactly so that it may be easily transported and stored.

Another object of this invention is to provide a collapsible light-weight childbirth chair having electronic monitoring apparatus.

The invention includes, briefly, a base having a seat portion and two leg portions extending outwardly therefrom, a first leg support hingedly attached to a first leg portion of the base and a second leg support hingedly attached to a second leg portion of the base, a first footrest adjustably attached to the first leg support and a second footrest adjustably attached to the second leg support, first leg support adjustment means for varying the inclination of the first leg support relative the base, second leg support adjusting means for varying the inclination of the second leg support relative the base, a backrest hingedly attached to the seat portion of the base and means for adjusting the inclination of the backrest relative the base.

It is an advantage of the present invention that the chair is relatively inexpensive, lightweight, and is compactly portable so that it may be easily transported to a childbirth site.

Another advantage of this invention is that the chair can help position a woman so that gravity assists rather than hinders the birthing process.

DESCRIPTION OF THE PREFERRED EMBODIMENT

Figures 1, 2:
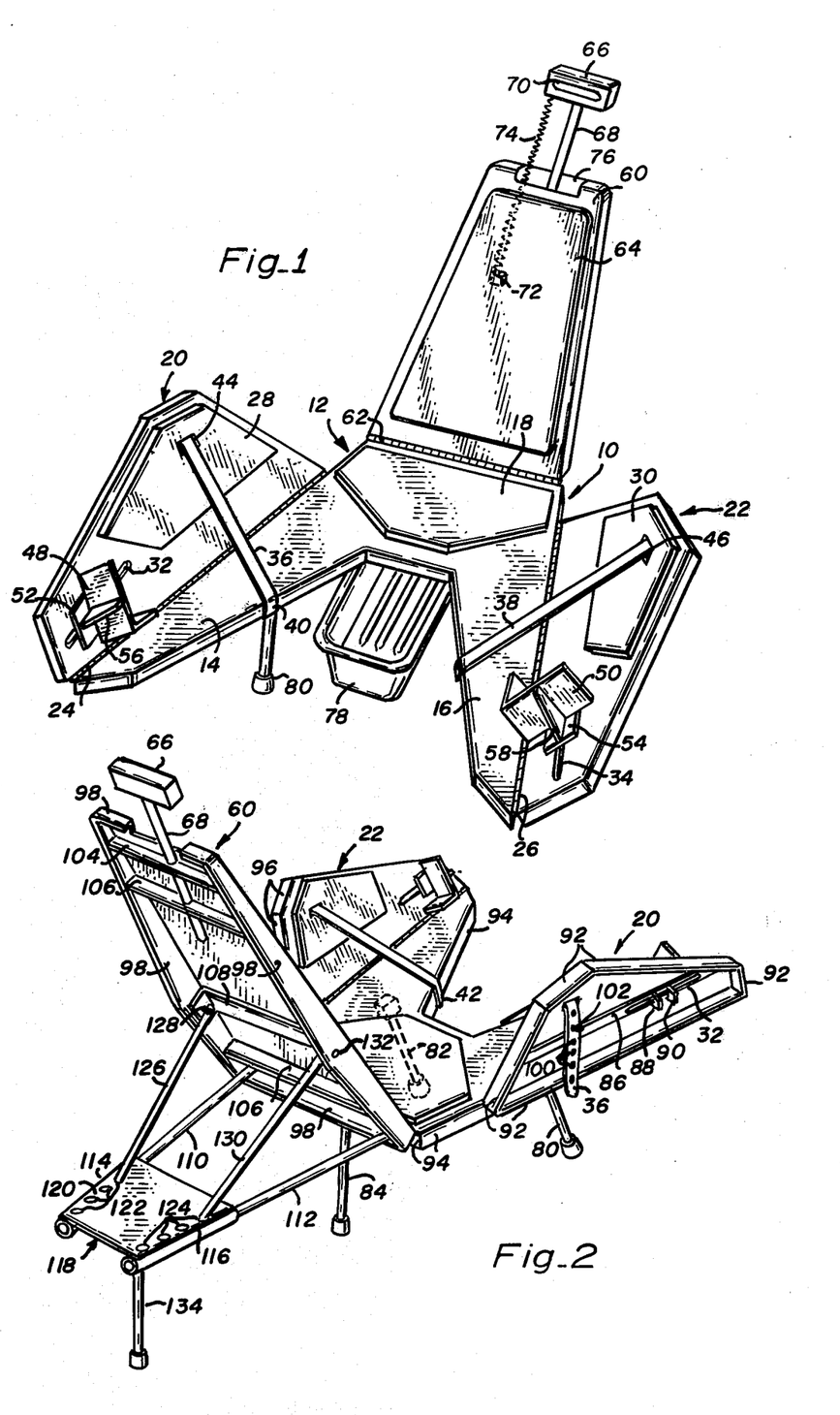
FIG. 1 is a perspective view of a childbirth chair in accordance with the present invention.
FIG. 2 is a perspective view showing the back of a childbirth chair as illustrated in FIG. 1.

In FIG. 1, a portable childbirth chair in accordance with the present invention is shown to include a base 10 having a seat portion 12 and two outwardly-extending leg portions 14 and 16.

Disposed upon seat portion 12 is a padding 18 which forms a comfortable seat for a woman sitting thereupon. The padding of the preferred embodiment is a tough, spongy, foamed-plastic material which is either attached to a flat surface of the base or which fits into a recess formed downwardly from an upper surface thereof.

A leg support 20 and a leg support 22 are attached to leg portions 14 and 16, respectively, by piano hinges 24 and 26, respectively. The leg supports are substantially triangular in shape, with their longest side being attached to the leg portions. The side of the leg supports proximate the seat portion of the base is shorter than the side of the leg supports distal the seat portion.

A section of the upper surface of leg supports 20 and 22 is provided with resilient paddings 28 and 30, respectively, of similar properties to previously discussed padding 18. These paddings, which provide a rest surface for the woman's knees and thighs, are also preferably adapted to reside in recesses formed from the upper supports of their respective leg supports.

Leg supports 20 and 22 are further provided with elongated slots 32 and 34, respectively, that function as tracks for a pair of footrests, which will be subsequently discussed.

Extending between leg portion 14 of the base and leg support 20 is an adjustment strap 36. Similarly, extending between leg portion 16 and leg support 22 is an adjustment strap 38. Strap 36 is permanently attached to leg portion 14 by a fastener such as a rivet 40 and strap 38 is attached to leg portion 16 by a fastener such as a rivet 42 (which can be seen in FIG. 2). Strap 36 extends through a slot 44 formed through leg support 20 to be adjustably attached to a lower surface thereof. In the same way, strap 38 extends through a slot formed in its leg support to be adjustably attached to a lower surface thereof.

By adjusting the lengths of the straps, it is possible to individually vary the inclination of the leg supports relative to the base. In the present embodiment, the inclination between the leg supports and the base may be varied over a range of 0 and 180 degrees, although in normal operation the angles of inclination would probably lie between 90 and 180 degrees. The adjustable attachment of the straps to the leg supports will be explained in greater detail during the discussion of FIG. 2.

Attached to leg supports 20 and 22 through slots 32 and 34, respectively, are footrests 48 and 50, respectively. The foot resting portion of footrests 48 and 50 is substantially L-shaped and is attached to a mounting block 52 or 54, respectively, by triangular bracing webs 56 or 58, respectively.

Attached to a bottom surface of each of the footrests are two studs, not shown in this figure, which extend through slots 32 and 34. The protruding ends of the studs have wing nuts threaded thereupon which, when tightened, hold the footrest in place along the slot. The wingnut attachments may be seen in FIGS. 2, 4 and 5.

A backrest 60 has, in this preferred embodiment, a generally trapezoidally shaped upper surface against which a woman undergoing labor may recline. The backrest of the present invention is attached along its longer parallel side to a rearward part of seat portion 12 by a piano-type hinge 62. Backrest 60 is of similar construction to the base and the leg supports in that downwardly depending from the upper surface are perimeter walls which create a hollow, unitized structure.

The backrest is also provided with a resilient padding 64 which is of similar construction and which is attached in much the same way as the previously discussed paddings.

An electronic monitoring apparatus 66 is attached to backrest 60 by a support means such as tube 68. The height of apparatus 66 above the backrest may be adjusted by changing the point of attachment between tube 68 and the backrest.

The apparatus has a display window 70 through which diagnostically helpful digital or analog displays may be seen. A monitor 72 to be placed on the woman's body is connected to apparatus 66 by a coiled telephone cord type cable 74.

An electronic monitoring apparatus seat 76 is formed at the top of the backrest by removing a suitably configured portion thereof so that apparatus 66, when fully retracted, can nestle therein.

Also seen in this figure is a receptacle 78 which is supported by a suspension rack attached to a lower surface of base 10. The receptacle may slide from under the base of the chair so as to capture any childbirth effluence, such as the afterbirth.

The terms "upper" and "lower" as applied to the base, leg supports and backrest refer to the relative positions of surfaces on those members when the chair is open, ready for use, and viewed as in FIG. 1. Furthermore, the terms "rearward" and "forward" as used in this specification are taken from the vantage point of the woman sitting in the chair, i.e., the backrest is attached to a rearward portion of the base. It is to be understood that the aforementioned terms are to be interpreted in this context to clarify the descriptive process, and are not to be interpreted as unalterable constants. For instance, when the chair is folded there is no reference for the terms "upper" and "lower" except by analogy to the open chair.

The childbirth chair as thus far described may be supported on any substantially flat surface such as a table top or the floor. However, and referring now to FIG. 2, it may be seen that the base of the chair is preferably supported by three legs 80, 82 and 84, where leg 80 supports leg portion 14, leg 82 supports leg portion 16, and leg 84 supports seat portion 12 of the base. A fourth leg which helps support the backrest of the chair will be discussed subsequently.

In this figure, the lower surface and general structure of leg support 20 may be more clearly seen. It is to be understood that leg support 22 is substantially a mirror image of the leg support 20, so that the discussion of the latter applies to the former.

Attached to the lower surface of leg support 20 is a frame member 84 through which slot 32 extends. The two studs of footrest 48 project through slot 32 and have wingnuts 88 and 90 threaded onto their ends. By loosening wingnuts 88 and 90, the footrest may slide along slot 32 of member 86 about 8 inches, in this preferred embodiment. When the footrest is correctly positioned wingnuts 88 and 90 may be tightened to clamp the footrest in place.

Also seen downwardly extending from the upper surface of leg support 20 are the aforementioned perimeter walls which are referenced generally with the numeral 92. Likewise downwardly depending from the base portion are perimeter walls referenced generally with the numeral 94, downwardly depending from the upper surface of leg support 22 are perimeter walls 96 and downwardly depending from backrest 60 are perimeter walls 98.

Referring again to leg support 20, it may be seen that the supporting strap 36 is provided with a plurality of eyelets 100 which may engage with a tang 102 attached to member 86. Thus, the inclination of leg rest 120 relative the base can be adjusted by disposing various ones of the eyelets upon the tang to lengthen or shorten the amount of strap extending between the leg portion of the base and the leg support.

An alternate construction for the strap attachment includes a friction buckle attached to member 86 through which the strap may be trained. The length of the strap may then be adjusted by pulling the web through the friction buckle in a well-known manner.

Also seen in FIG. 2 is the attachment of electronic monitoring apparatus support rod 68 to the lower rear surface of backrest 60. A pair of stiffening webs 104 and 106 are attached to the lower surface of backrest 60 to extend between opposing sidewalls 98. Formed through webs 104 and 106 are bores of a diameter slightly less than that of rod 68. Rod 68 is disposed through the bores and is held firmly therein by the inherent resiliency of the web material. The backrest is further strengthened by a web 106 and by a support bracket 108 whose function will be discussed subsequently.

Extending from the base through a portion of wall 94 proximate the rear of the seat portion are a pair of convergingly angled backrest support frame members 110 and 112. The ends of these members are disposed within tubes 114 and 116, respectively, of an endplate member 118.

Endplate member 118 further includes a trapezoidally-shaped plate 120 which is attached, preferably by welding, to tubes 114 and 116 along two nonparallel sides. A first plurality of holes 122 are formed along the plate 120/tube 114 juncture and a second plurality of holes 124 are formed along the plate 120/tube 116 juncture.

A first backrest support rod 126 is pivotally attached to one leg of U-shaped bracket 108 by a fastener such as rivet 128. Similarly, a second backrest support rod 130 is attached to the other leg of U-shaped bracket 108 by a fastener such as rivet 132. The free end of rod 128 may be inserted into one of holes 122 and the free end of rod 130 may be inserted into one of the holes 124.

By inserting the ends of rods 126 and 130 into one of holes 122 and 124, respectively, the inclination of the backrest relative the base may be adjusted. For instance, if the rods are placed in holes proximate the shorter parallel side of plate 120, the inclination of the backrest is relatively slight while if the rods are placed in holes proximate the longer parallel side of plate 120, the inclination is relatively great.

Furthermore, rods 126 and 130 may be folded against the back of backrest 60 so that the backrest may lie flat against the support frame members. Therefore, in the present embodiment, five inclinations for the backrest relative the base are possible between approximately 0 and 60 degrees.

Supporting end plate member 118 is a fourth leg 132. The actual attachment of the leg to the lower surface of plate 120 will be discussed with reference to a later figure.

Figures 3, 4:
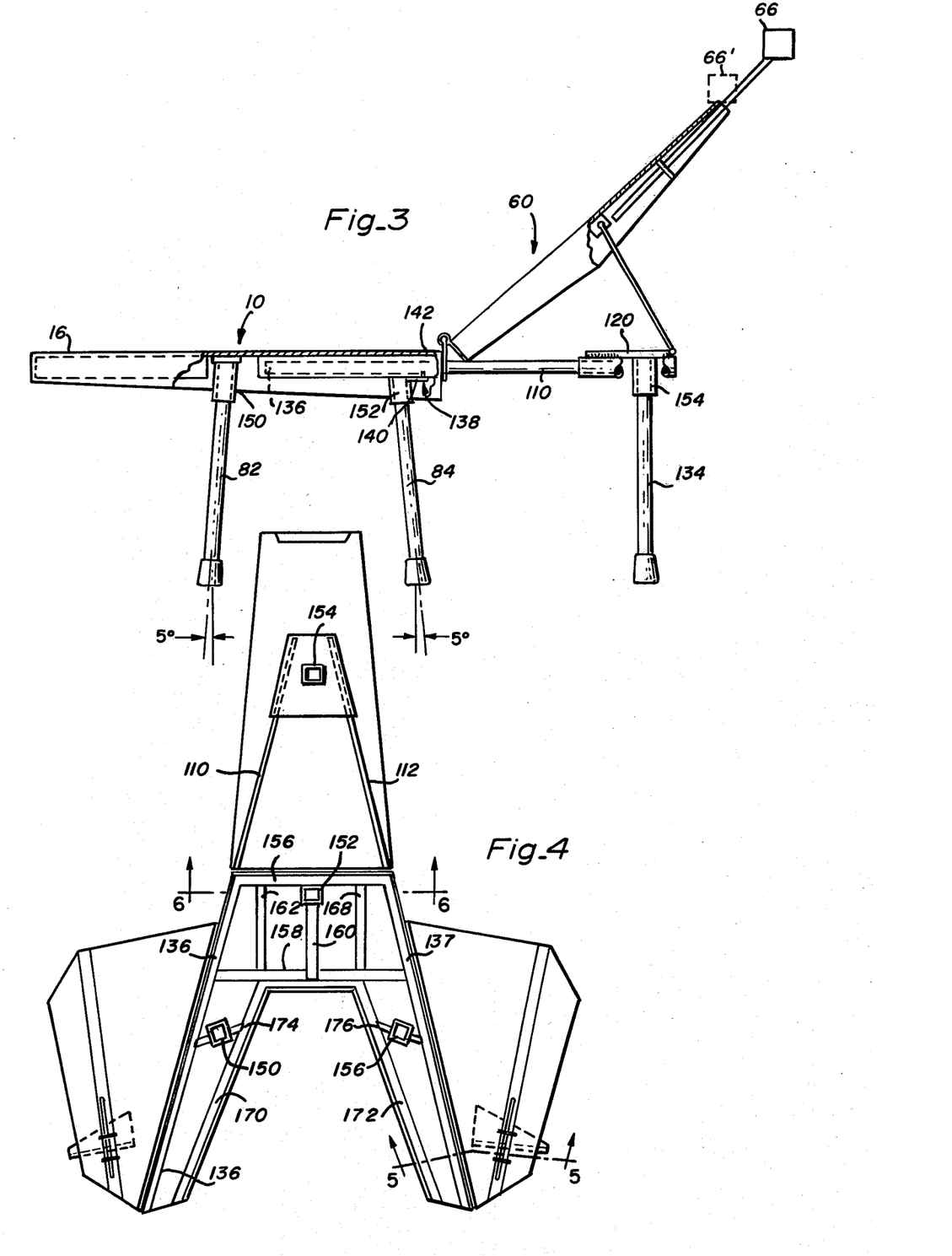
FIG. 3 is a partially broken side elevational view of a childbirth chair as shown in FIG. 1.
FIG. 4 is a bottom plan view of a childbirth chair as shown in FIG. 1.

Referring now to FIG. 3, the chair is shown in a side elevational view with parts of various members broken away to more clearly show the internal structure.

Attached to the lower surface of base 10 is a hollow frame member 134 which extends through the seat portion and down leg portion 16. Similarly, a hollow frame member 136, which cannot be seen in this figure, extends through the seat portion and down leg portion 14. Backrest support frame member 110 extends telescopically into frame member 134 and freely slides therein unless inhibited by a detent mechanism 138 which includes a flexure 140 having a pin 142 attached to one end thereof and being attached at its other end to base frame member 136. Flexure 140 urges pin 142 through an aperture in member 136 to engage with one of a plurality of apertures formed in member 110.

Analogously, member 112, not seen in this figure, is telescopically disposed within base frame member 136 and is free to slide therein unless inhibited by detent member 144 including a flexure 146 having a pin 148 attached to one end and which is attached to member 136 at its other end. The pin can extend through an aperture in member 136 to engage with one of a plurality of apertures formed in member 112.

In the preferred embodiment legs 83, 84 and 134 are not permanently attached to the chair, but are retained in position by sleeves 150, 152 and 154, respectively. Similarly, leg 80 is retained in position by a sleeve 156, not shown in this figure.

Sleeve 154 is attached substantially perpendicularly to plate 120 so that leg 134 is retained generally perpendicular to the support surface. Sleeves 150, 152 and 156 are attached to a lower surface of base 10 at a slight angle thereto so as to position legs 80-84 into a braced, three-point support for the base of the chair. In this preferred embodiment, legs 80 and 82 angle about 5 degrees forwardly and about 5 degrees outwardly, and leg 84 angles about 5 degrees rearwardly.

Also seen in this figure is the electronic monitoring apparatus which is shown extended at 66 and retracted at 66'. When retracted, the apparatus compactly nestles into seat 76.

Referring now to the bottom plan view of FIG. 4, it may be seen that members 134 and 136 extend from the end of the seat portion down along opposite edges of the base. They are transversely connected proximate the seat portion of the base by cross members 156 and 158, which are in turn connected by a brace 160. Also extending between members 156 and 158 are a pair of suspension members 162 and 168 formed from "C" channel stock for supporting receptacle 78.

Extending along the interior edge of leg portion 16 is a structural member 170 which is attached at one end to member 136 and attached at its other end to cross bar 158. Similarly, extending along the interior edge of leg portion 14 is a structural member 172 which is attached at one end to member 136 and attached at its other end to cross bar 158. Connected between members 134 and 170 is a short, rigid metal strap 174 to which sleeve 150 is fastened and connected between member 136 and 172 is a short, rigid metal strap 76 to which sleeve 156 is fastened. Sleeve 152 is attached to brace 160.

Thus, the various members attached to the bottom of the base form a rigid yet lightweight A-shaped frame for strengthening the base.

Figure 5:
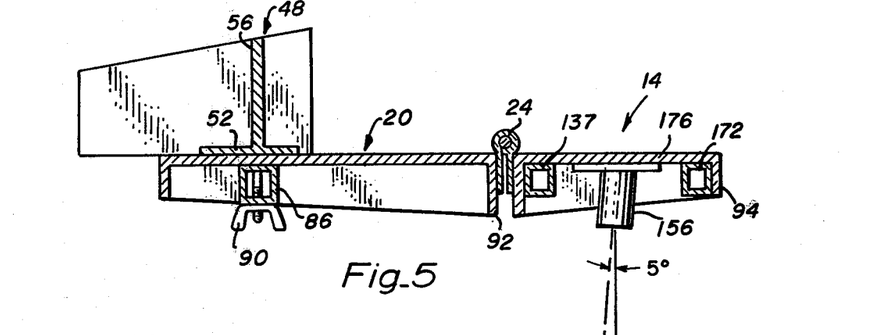
FIG. 5 is an inverted cross-sectional view taken along line 5—5 of FIG. 4.

In FIG. 5, leg portion 14 is seen to be attached to leg support 20 by a piano hinge 24. Strap 176 extends between members 137 and 172 to support sleeve 156 at an angle of approximately 5 degrees relative thereto. Also seen is the cross section of member 86 through which a stud of footrest 48 extends to be fastened in place by a wingnut 90. Seen in cross section are mounting blocks 52 and web 56 which brace and support footrest 48.

Figures 6, 7:
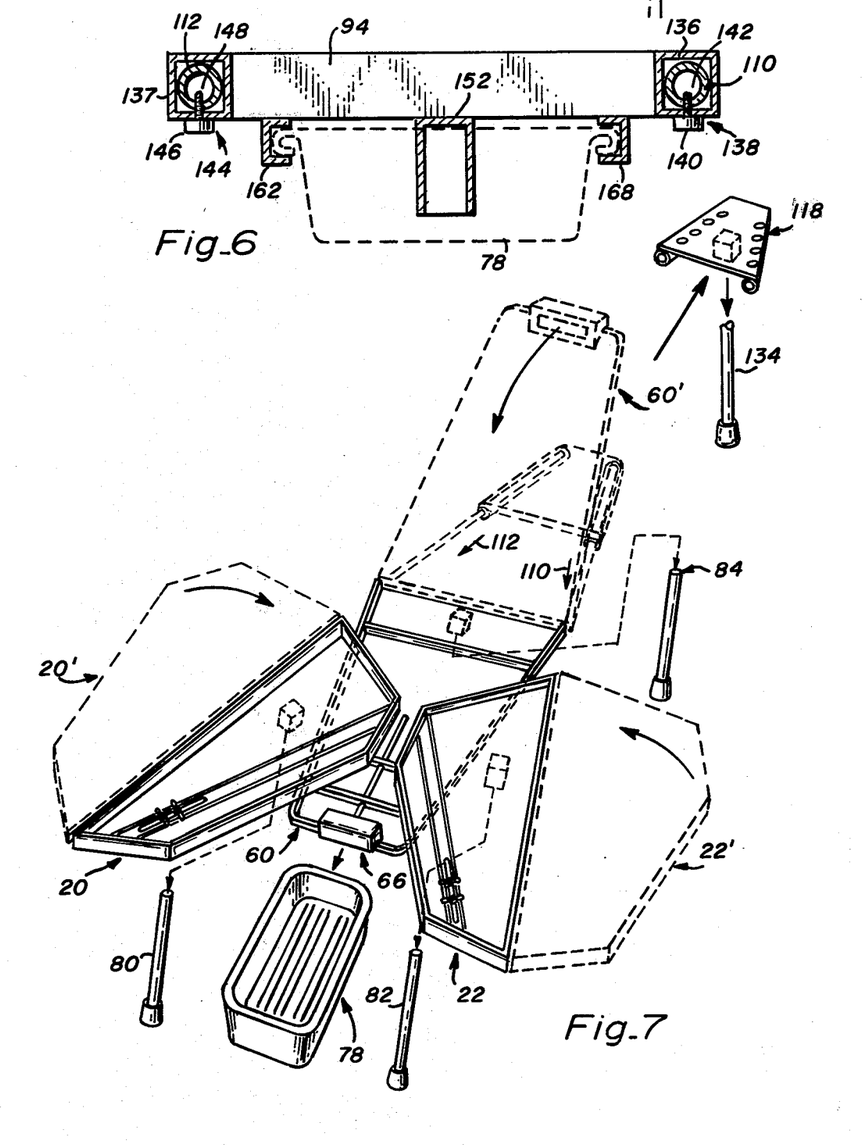
FIG. 6 is an inverted cross-sectional view taken along line 6—6 of FIG. 4.
FIG. 7 is a perspective view of a childbirth chair as shown in FIG. 1 illustrating a method for compactly collapsing the chair so that it may be easily transported or stored.

In FIG. 6, "C" channel members 162 and 168 are shown supporting a phantom receptical 78'. Opposing lips of the receptical are disposed in the "C" channel suspension members and are free to slide therealong so that the receptacle may be retracted under the seat portion for storage or may be extended forwardly to catch any effluence of the birthing process.

Also seen in cross section, is sleeve 152 and details of the detent mechanisms which index backrest support frame members 110 and 112 within members 134 and 136, respectively.

As seen more clearly in this figure, pin 148 extends through both an aperture in member 137 and an aperture in member 112 and pin 132 extends through aligned apertures in members 136 and 110. Since both members 110 and 112 have a plurality of apertures formed along their length, the amount that they extend rearwardly from the base may be adjusted.

FIG. 7 shows how the portable childbirth chair of the present invention may be disassembled and folded for compact storage and so as to be more easily transported. In a preferred method of disassembly, the tray and legs are removed as indicated by dashed lines, members 110 and 112 are telescoped into the base by disabling detent members 138 and 144, end plate 118 is removed, rods 126 and 130 are folded against the "lower" surface of the backrest, and electronic monitoring apparatus 66 is retracted into its lowest position so as to nestle into the seat formed in the top portion of the backrest. The backrest may be then folded over the base of the chair, and the two leg rests folded over the backrest. Loose components, such as the legs and the end plate member, may be placed in the tray and/or separately bagged.

Figure 8:
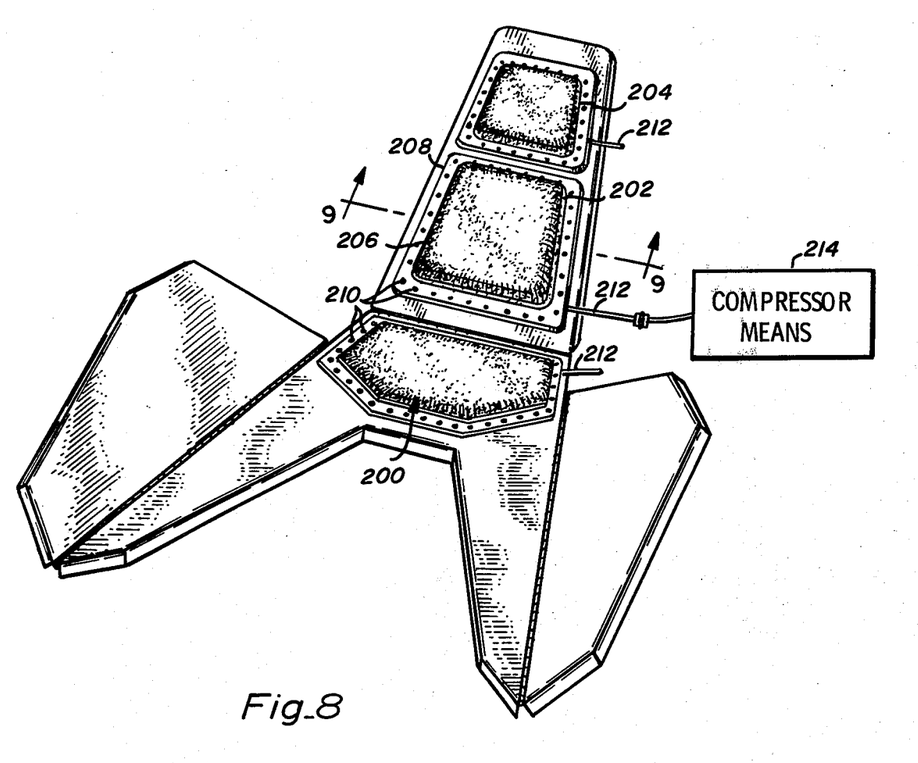
FIG. 8 is a perspective view of an alternate embodiment for a childbirth chair in accordance with the present invention.
Figure 9:
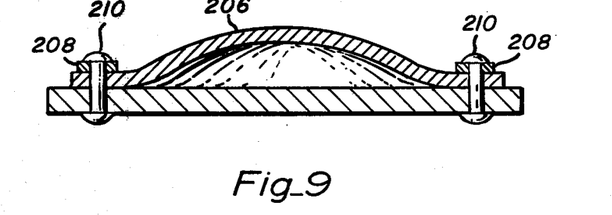
FIG. 9 is a sectional view taken along line 9—9 of FIG. 8.

In FIGS. 8 and 9, an alternate embodiment for the paddings found on the base and backrest is shown. In this embodiment, there is a padding member 200 on the base and a pair of padding members 202 and 204 on the backrest. Although only padding member 202 will be specifically discussed, it is to be understood that the construction of members 202 and 204 are similar with like reference numerals referring to like components.

Member 202 includes a flexible, nonporous material 206 which is clamped around its periphery by a flange 208 attached to the chair by a plurality of rivets 210. Extending through flexible material 206 is a valve 212 by which the padding member may be inflated or deflated by forcing air between material 206 and the upper surface of the chair. A compressor means 214 may also be optionally provided to facilitate the inflation of the member.

Thus, the firmness and/or contour of the padding members 200-204 may be adjusted to accommodate various situations occurring during the childbirth process or to more comfortably adjust the chair to the contours of the particular woman undergoing childbirth.

Figure 10:
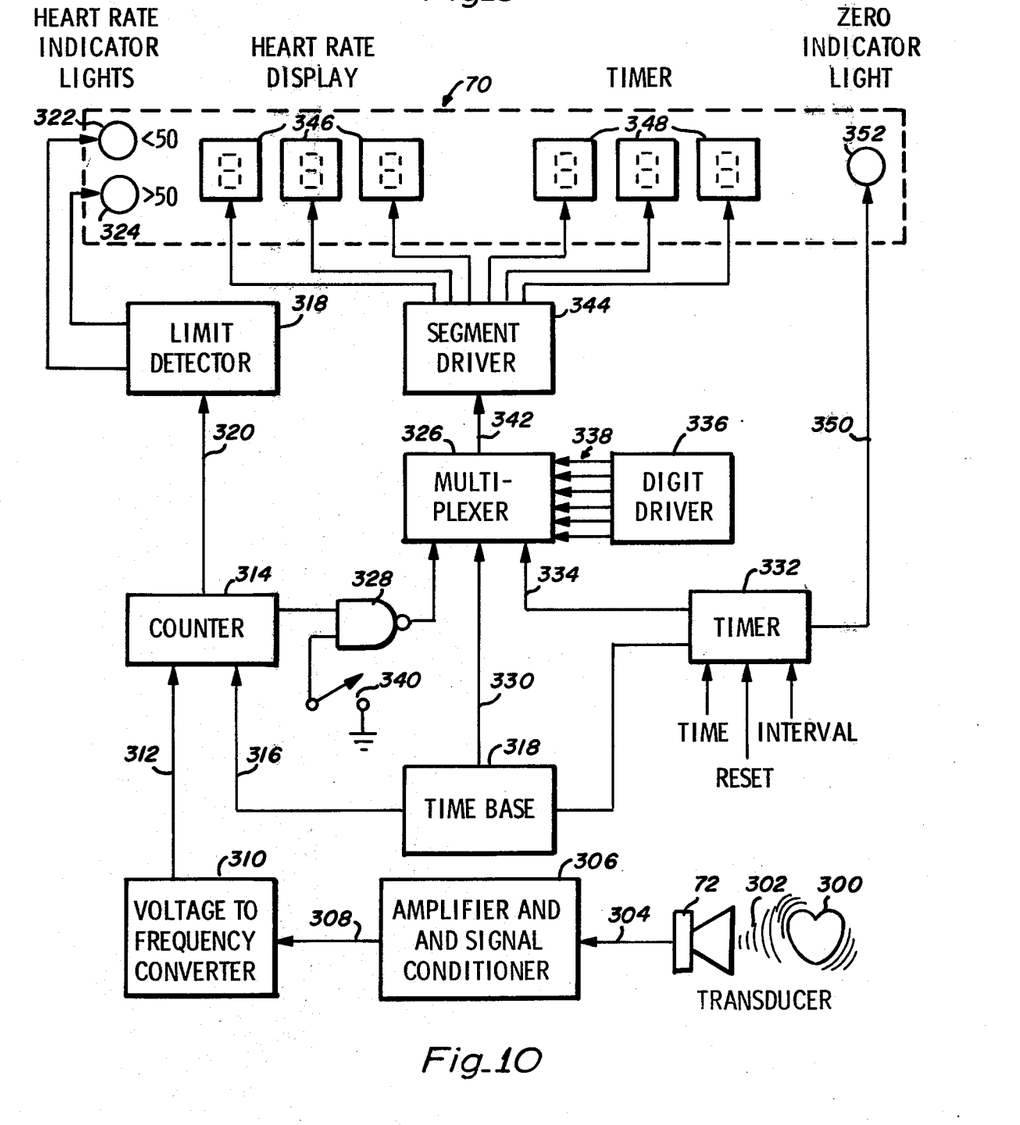
FIG. 10 is schematic and block diagram of an embodiment for the electronic monitoring apparatus shown in FIG. 1.

In FIG. 10, a schematic and block diagram illustrates a preferred embodiment for a combination fetal heart monitor and digital timer which is included in the electronic monitoring apparatus 66. Broken line 300 represents display window 70 of the apparatus.

The fetal heart monitor portion of the circuit includes a transducer 302, an amplifier and signal conditioner 304, a voltage-to-frequency converter 306, a counter 308, a limit detector 310, two display lights 312 and 134, and three 7-segment displays 316, 318 and 320.

The timer portion of the circuit includes a timer 322, an indicator light 324, and three 7-segment displays 326, 328 and 330.

Components shared by both the fetal heart monitor and the timer include a power supply, not shown, a time base 332, a multiplexer 334, a digit driver 336, and a segment driver 338.

In the fetal heart rate portion of this circuit, transducer 302 is responsive to audio vibrations produced by the fetus' heart 340 and develops an electrical signal on a line 342 proportional thereto. A typical frequency of the signal produced on line 342 would be between fifty and several hundred Hertz.

Amplifier and signal conditioner 304 is responsive to the signal on line 342 and outputs a regulated DC voltage on a line 344 having an amplitude proportional to the frequency of the signal found on line 342.

Voltage-to-frequency converter 306 inputs the DC voltage found on line 344 and outputs a signal on a line 346 having a frequency proportional thereto.

Counter 308 is responsive to the signal found on line 346 and to time base 332 by means of a line 348 and is operative to output a digital signal on lines 350 which represents the fetal heart rate in beats per minute.

Limit detector 310 is responsive to the digital signal on line 350 and is operative to develop an indicator light driving potential on a line 352, if the fetal heart rate is less than 50 beats per minute and an indicator light driving potential on a line 354 if the fetal heart rate is greater than 50 beats per minute. Thus, display lights 312 and 314 indicate to a person assisting a woman during childbirth whether the fetal heart rate is becoming dangerously low. Line 350 is also connected to a first input of a two-input NAND gate 356. The other input of the NAND gate is connected to a grounding switch 358 by line 360. The output of NAND gate 356 is connected to a line 362.

When switch 358 is open, a signal will be developed on line 362 which is the inverse of the signal found on line 350. When switch 358 is closed the signal on line 362 is locked into a high logic state and is not responsive to the signal on line 350.

Multiplexer 334 is responsive to the signal developed on line 362, to the time base by means of a line 364 and to digit driver 336 by means of a plurality of lines 366.

Digit driver 336, in part, decides which one of the three 7-segment indicators of the heart rate display is to be energized. Multiplexer 334 develops an output signal on line 368 by internally switching the digital signal found on line 362 to the appropriate digits. Segment driver 338 decodes the signal on line 368 and appropriately drives the segments of the digit selected by digit driver 336 by means of one of lines 370.

The operation of the fetal heart monitor portion of the electronic monitoring apparatus circuit is believed to be as follows. Transducer 302 produces a signal including peaks corresponding to the fetal heart beat. Also generated by the transducer, however, is a great deal of noise due to accoustical interferences such as the mother's heart beat, body noises, and ambient interference. Amplifier and signal conditioner 304 first cleans the signal developed by the transducer and then converts the clean signal into a DC potential which is proportional to the frequency of the fetus' heart beat. Voltage-to-frequency converter 306 converts this DC potential to a frequency signal proportional thereto. The frequency produced by converter 306 is a multiple of the fetus' heart rate so that a rapid fetal heart rate display update in beats per minute can be made.

For instance, if converter 306 produced a signal of a frequency six times that of the fetal heart rate, and heart rate display could be updated every 10 seconds rather than every minute.

Counter 308 counts the zero excursions of the signal produced by converter 306 to determine the fetal heart rate. Limit detector 310 compares the fetal heart rate to a cut-off rate of 50 beats per minute and lights the appropriate indicator light. If switch 358 is open, the multiplexer and segment driver also digitally display the heart rate as previously explained.

The timer portion of the electronic monitoring apparatus circuit has a timer 322 connected to time base 322 from which it derives clocking pulses by a line 372. Timer 322 can be operated in any of three modes as set by lines 374, 376, and 378. If line 374 is energized, the timer performs as a digital clock by developing a digital time signal on a line 380 which is processed by the multiplexer and segment driver to illuminate the timer display digits 326–330. If line 376 is energized, timer 332 performs as a stop watch by first zeroing digits 326–330 and then counting upwards by seconds. If line 378 is energized timer 322 performs as a countdown clock by first setting digits 326–330 to a predetermined interval, such as three minutes, and then counting down to zero. When the timer display does read zero, timer 322 develops an indicator light driving signal on a line 382 to illuminate zero indicator light 324.

Although the present invention has been described above with reference to a particular preferred embodiment, it is to be understood that modifications thereof will be obvious to those skilled in the art. For instance, in the preferred embodiment, the base, leg rests and backrest are formed of a plastic such as ABS to create a hollow, unitized structure and are strengthened with aluminum frame members attached to their lower surfaces by adhesive, rivets, etc. Alternatively, those members could be fashioned in solid form from wood, honeycomb, aluminum, etc. It is therefore intended that the appended claims be interpreted to cover all such modifications as fall within the true spirit and scope of the invention.

What is claimed is:

1. A portable childbirth chair comprising:

a base having a seat portion and two outwardly extending leg portions:
a first leg support hingedly attached to one side of a first of said leg portions, and rotatable between a leg support position and a folded position;
first means for adjusting the inclination of said first leg support relative to said base when it is in its leg support position;
first footrest means;
first means for attaching said footrest means to said first leg rest;
a second leg support hingedly attached to one side of the second of said leg portions and rotatable between a leg support position and a folded position;
second means for adjusting the inclination of said second leg support relative to said base when it is in its leg support position;
second footrest means;
second means for attaching said second footrest means to said second leg support;
a backrest hingedly attached to the seat portion of said base and rotatable between a back support position and a folded position; and
third means for adjusting the inclination of said backrest relative said base when it is in its back support position;
whereby when the chair is in use, a woman undergoing labor may sit upon said seat portion, place her feet upon said footrests with her legs supported by said leg supports and recline against said backrest, and when said chair is not in use the leg supports and backrest may compactly fold over said base so that the chair may be more easily stored and transported.

2. A portable childbirth chair as recited in claim 1 wherein:
said first means for attaching includes
a first guide means disposed along said first leg support, and
a first clampable slide assembly having a first member rigidly attached to said first footrest means, and second member cooperating with said first member to form a first clamping means which, when disabled, loosely engages said first guide means and, when enabled, rigidly clamps to said first guide means; and
said second means attaching includes
a second guide means disposed along said second leg support,
a second clampable slide assembly having a first member rigidly attached to said second footrest means, and a second member cooperating with said first member to form second clamping means which, when disabled, loosely engages said second guide means and, when enabled, rigidly clamps to said second guide means;
whereby said first and second footrests may individually travel along the lengths of their respective guide means when said clamping means are disabled and are fixed in position along their respective guide means when said clamping means are enabled.

3. A portable childbirth chair as recited in claim 2 wherein:
said first guide means includes a first elongated slot formed through said first leg support;
said first member of said first slide assembly includes a first threaded stud means attached at a first end to said first footrest means and positioned so that a second end thereof protrudes through said first slot;
said second member of said first slide assembly includes a first nut means threaded onto the second end of said first stud means and forming said first clamping means therewith whereby tightening said first nut means on said first stud enables said first clamping means and where loosening said first nut means on said first stud disables said first clamping means;
said second guide means includes a second elongated slot formed through said second leg support;
said first member of said second slide assembly includes a second threaded stud means attached at a first end to said second footrest means and positioned so as to protrude through said second slot; and
said second member of said second slide assembly includes a second nut means threaded onto the second end of said second stud means and forming said second clamping means therewith, whereby tightening said second nut means on said second stud enables said second clamping means and where loosening said second nut means on said second stud disables said second clamping means.

4. A portable childbirth chair as recited in claim 1 wherein:
said first adjustment means includes
a first elongated flexible strap means attached proximate a first end to said first leg portion, and
first means for adjustably fastening a portion of said first strap means lying between a first end and a second end to said first leg support; and
said second adjustment means includes
a second elongated flexible strap means attached proximate a first end to said second leg portion, and
second means for adjustably fastening a portion of said second straps lying between said first end and a second end to said second leg support;
whereby the inclinations of said leg supports relative the base are independently adjustable by varying the length of the first and second straps.

5. A portable childbirth chair as recited in claim 4 wherein:
said first means for adjustably fastening includes
a first tang attached to said first leg support, and
a first plurality of eyelets formed along the length of said first strap means; and
said second means for adjustably fastening includes
a second tang attached to said second leg support, and
a second plurality of eyelets formed along the length of said second strap means;
whereby said tangs can engage any one of their respective plurality of eyelets as to adjust the length of the strap extending between the leg portion and the leg support.

6. A portable childbirth chair as recited in claim 5 wherein said first leg support is provided with a first aperture through which said first strap means is trained and where said first tang is attached to a surface of said first leg support proximate said first aperture; and
said second leg support is provided with a second aperture through which said second strap means is trained and where said second tang is attached to a surface of said second leg support proximate said second aperture.

7. A portable childbirth chair as recited in claim 1 wherein said third means for adjusting includes:
a first backrest support frame member extending outwardly from said seat portion in a direction substantially opposite to said first leg portion;
a second backrest support frame member extending outwardly from said seat portion in a direction substantially opposite to said second leg portion;
and endplate member for connecting the ends of said first and second backrest support frame members together, said endplate member being provided with a first and a second plurality of holes;
a first elongated backrest support rod pivotally attached at a first end to said backrest and adapted to engage a second end thereof with one of said first plurality of holes; and
a second elongated backrest support rod pivotally attached at a first end to said backrest and adapted to engage a second end thereof with one of said second plurality of holes;
whereby the inclination of said backrest relative said base may be adjusted by placing the second ends of said support rods in various ones of said pluralities of holes.

8. A portable childbirth chair as recited in claim 7 wherein said endplate member includes:
a plate portion formed with at least two edges;
a first tube portion having an internal diameter slightly larger than the external diameter of said first backrest support frame member and fastened to a first edge of said plate; and
a second tube portion having an internal diameter slightly larger than the external diameter of said second backrest support frame member and fastened to a second edge of said plate;
whereby said end plate portion connects said backrest support frame members when an end of said first backrest support frame member is disposed within said first tube portion and an end of said second backrest support frame member is disposed within said second tube portion.

9. A portable childbirth chair as recited in claim 7 wherein said first and said second backrest support frame members telescope into said base.

10. A portable childbirth chair as recited in claim 9 further comprising:
a first detent mechanism attached to said base for engaging apertures formed along the length of said first backrest support frame member; and
a second detent mechanism attached to said base for engaging apertures formed along the length of said second backrest support frame member;
whereby said first and second detent members allow the projecting length of said first and second backrest support frame members, respectively, to be varied.

11. A portable childbirth chair as recited in claim 10 wherein said first detent mechanism includes:
a first elongated flexure attached proximate a first end to said base; and
a first pin attached proximate a second end of said flexure; and
a second detent mechanism includes:
a second elongated flexure attached proximate a first end to said base, and
a second pin attached proximate a second end of said flexure;
whereby said first and second pins are urged into said apertures of said backrest support frame members by said flexures.

12. A portable childbirth chair as recited in claim 1 wherein:
said base, said first leg support, said second leg support and said backrest each include:
a surface means defining an upper surface and a lower surface,
wall means forming a perimeter around said surface means and downwardly extending from said upper surface, and
frame means attached to said lower surface;
whereby said base, said first leg support, and second leg support and said backrest form lightweight, hollow and unitized structures and are braced by said frame means for enhanced rigidity and strength.

13. A portable childbirth chair as recited in claim 12 wherein said surface means and said wall means are constructed from a plastic material and said frame means is constructed from aluminum tubing.

14. A portable childbirth chair as recited in claim 1 wherein said hinged attachments of said leg supports and said backrest are piano-type hinges.

15. A portable childbirth chair as recited in claim 1 further comprising:
a first padding means disposed upon said seat portion,
a second padding means disposed upon said first leg support,
a third padding means disposed upon said second leg support, and
a fourth padding means disposed upon said backrest,
whereby said padding means provide cushioning for the portions of a woman's body which contact the chair.

16. A portable childbirth chair as recited in claim 15 wherein said first, second, third and fourth padding means reside in recesses formed in said seat portion, first leg support, second leg support and backrest, respectively.

17. A portable childbirth chair as recited in claim 15 wherein said first, second, third and fourth padding means are formed from a spongy, foamed, thermoplastic material.

18. A portable childbirth chair as recited in claim 15 wherein:
said first padding means includes
a first flexible, nonporous sheet of material disposed upon said seat portion,
a first flange means disposed over said first sheet so as to cover the edges but not central portions thereof,
first means fastening said first flange means to said seat portion so that a first internal volume is defined between said first sheet and said seat portion, and
first valve means providing communication between said first internal volume and the ambient environment; and
said fourth padding means includes
a second flexible, nonporous sheet of material disposed upon lower portion of said backrest,
a second flange means disposed over said second sheet so as to cover the edges but not the central portions thereof, second means fastening said second flange means to said backrest so that a second internal volume is defined between said second sheet and said backrest, and second valve means providing communication between said second internal volume and the ambient environment, and a third flexible, nonporous sheet of material disposed on an upper portion of said backrest, a third flange means disposed over said third sheet so as to cover the edges but not the central portions thereof, third means fastening said third flange means to said backrest so that a third internal volume is defined between said third sheet and said backrest, and third valve means providing communication between said third internal volume and the ambient environment;

whereby said first, second and third internal volumes may be increased or decreased by injecting or removing air through said valve means and thus expanding or contracting, respectively, said sheets.

19. A portable childbirth chair as recited in claim 18 further comprising:
   a compressor means for injecting air into said internal volumes through said valves.

20. A portable childbirth chair as recited in claim 1 further comprising leg means for supporting said base over a substantially flat surface.

21. A portable childbirth chair as recited in claim 20 wherein said leg means includes:
   a first leg removably attached to a lower surface of said base portion,
   a second leg removably attached to a lower surface of said first leg portion,
   a third leg removably attached to a lower surface of said second leg portion; and
   a fourth leg removably attached to a lower surface of said endplate member.

22. A portable childbirth chair as recited in claim 1 further comprising:
   a receptacle means; and
   means suspending said receptacle means from a lower surface of said base so that the receptacle may be supported entirely under said seat portion or may be supported so that at least a portion thereof extends forwardly of said seat portion between said leg portions.

23. A portable childbirth chair as recited in claim 22 wherein said means suspending includes:
   a pair of facing "C" channel members attached to a lower surface of said base, and
   said receptacle includes a protruding lip which slidingly engages with said "C" channel members.

24. A portable childbirth chair as recited in claim 1 further comprising:
   an electronic monitoring apparatus; and
   means for connecting said monitoring apparatus to a rearward portion of said backrest.

25. A portable childbirth chair as recited in claim 24 wherein said means for connecting includes a support tube attached to said monitoring apparatus proximate a first end and slideably attached to said backrest between a second end and said first end.

26. A portable childbirth chair as recited in claim 24 wherein said electronic monitoring apparatus includes:

a fetal heart monitor having
   a transducer for converting audio frequency compression waves from a fetus's heartbeat into a first electrical signal whose frequency is proportional to the heartbeat rate,
   an amplifier and signal conditioner responsive to said first signal and operative to produce a DC potential proportional to said frequency,
   a voltage to frequency converter responsive to said DC potential and operative to produce a second signal whose frequency is proportional to said DC potential and thus to said fetus' heart rate, whereby said second signal has a frequency that is a multiple of the frequency of said first signal,
   a time base for producing timing pulses,
   a counter responsive to both said timing pulses and said second signal and operative to produce a first digital signal representative of said fetus' heart rate in beats per minute,
   a limit detector responsive to said first digital signal and operative to produce a first indicator light driving potential if said digital signal is below a predetermined value and to produce a second indicator light driving potential if said digital is above said predetermined value,
   a first indicator light responsive to said first driving potential and for indicating that said fetus' heart rate is below said predetermined value,
   a second indicator light responsive to said second driving potential and for indicating that said fetus' heart rate is above said predetermined value,
   a heart rate display on-off switch, for producing an on-off signal,
   a NAND gate responsive to said on-off signal and to said first digital signal and operative to produce an inverted signal which is an inversion of said digital signal if said on-off siganl is on and is at a fixed potential if said on-off signal is off,
   a digit driver for producing digit driving potentials,
   a multiplexer responsive to said inverted signal, said timing pulses and said digit driving potentials and operative to produce heart rate display segment driving potentials, and
   a heart rate display responsive to said segment driving potential and for displaying the fetus' heart rate in beats per-minute; and a timer having
   a time base for producing time pulses,
   a timer operable in a time, reset or interval mode that is responsive to said timing pulses and operative to produce a second digital signal, and is further operative to produce a third indicator light driving potential when said second digital signal is zero,
   a zero indicator light responsive to said third potential,
   a digit driver for producing digit driving potentials,
   a multiplexer responsive to said digit driving signal, said timing pulses and said digit driving potentials, and operative to produce a multiplexed time display signal,
   a segment driver responsive to said multiplexed time display signal and operative to produce time display segment driving potentials, and
   a timer display responsive to said segment driving potentials and for displaying a time indication.

* * * * *